United States Patent
Illenberger et al.

(10) Patent No.: US 11,672,214 B2
(45) Date of Patent: Jun. 13, 2023

(54) BIOREACTOR AND USE THEREOF, METHOD FOR PRODUCING AN ORGANIC NUTRIENT SOLUTION, ORGANIC NUTRIENT SOLUTION, SUBSTRATE MATERIAL AND USE THEREOF FOR CULTIVATING PLANTS

(71) Applicant: Jassen—Kunststoffzentrum GmbH—Apparatebau, Zuschnitte und Formung, Steinen (DE)

(72) Inventors: Bernhard Illenberger, Steinen (DE); Hartmut Jassen, Steinen (DE)

(73) Assignee: Jassen—Kunststoffzentrum GmbH—Apparatebau, Zuschnitte und Formung, Steinen (DE)

( * ) Notice: Subject to any disclaimer, the term of this patent is extended or adjusted under 35 U.S.C. 154(b) by 402 days.

(21) Appl. No.: 16/955,979

(22) PCT Filed: Dec. 13, 2018

(86) PCT No.: PCT/EP2018/084682
§ 371 (c)(1),
(2) Date: Jun. 19, 2020

(87) PCT Pub. No.: WO2019/121285
PCT Pub. Date: Jun. 27, 2019

(65) Prior Publication Data
US 2020/0305370 A1   Oct. 1, 2020

(30) Foreign Application Priority Data
Dec. 22, 2017 (DE) .......................... 102017131089.4

(51) Int. Cl.
*A01G 31/02* (2006.01)
*C05F 17/90* (2020.01)
(Continued)

(52) U.S. Cl.
CPC .............. *A01G 31/02* (2013.01); *C05F 17/20* (2020.01); *C05F 17/40* (2020.01); *C05F 17/90* (2020.01);
(Continued)

(58) Field of Classification Search
CPC ......... A01G 31/02; C05F 17/20; C05F 17/40; C05F 17/90; C12M 1/04; C12M 25/16;
(Continued)

(56) References Cited

U.S. PATENT DOCUMENTS 3,728,254 A * 4/1973 Carothers ................. C02F 3/06
210/195.3
3,779,906 A   12/1973 Levin
(Continued)

FOREIGN PATENT DOCUMENTS

CN   87207429   5/1988
CN   102826652   12/2012
(Continued)

*Primary Examiner* — Fred Prince
(74) *Attorney, Agent, or Firm* — Volpe Koenig

(57) ABSTRACT

A bioreactor (1, 2, 3) and its use for the conversion of organic residual and/or waste materials into an organic nutrient solution with a proportion of at least 10% plant-accessible mineralised nitrogen relative to the total nitrogen content of the nutrient solution, with a reaction tank (5), where the reaction tank (5) has an input feed (6) through which suspension (4) can be introduced into the reaction tank (5), and where the reaction tank (5) has an outlet feed (7), through which the suspension (4) can be discharged from the reaction tank (5), where the carrier element (10) has at least one inner and one outer settlement surface (11), on which ammonifying and/or nitrifying bacteria can collect.

15 Claims, 2 Drawing Sheets

(51) Int. Cl.
*C05F 17/40* (2020.01)
*C05F 17/20* (2020.01)
*C12M 1/00* (2006.01)
*C12M 1/04* (2006.01)
*C12M 1/12* (2006.01)
*C12M 1/40* (2006.01)

(52) U.S. Cl.
CPC ............ *C12M 1/04* (2013.01); *C12M 1/40* (2013.01); *C12M 25/02* (2013.01); *C12M 25/16* (2013.01); *C12M 29/02* (2013.01); *C12M 29/04* (2013.01); *C12M 47/00* (2013.01); *Y02A 40/20* (2018.01); *Y02P 20/145* (2015.11); *Y02W 10/10* (2015.05); *Y02W 30/40* (2015.05)

(58) Field of Classification Search
CPC ...... C12M 29/02; C12M 29/04; C12M 47/00; C12M 25/02; C12M 1/40; Y02A 40/20; Y02P 20/145; Y02W 10/10; Y02W 30/40
USPC ................ 47/62 R, 62 A, 62 C, 62 E, 62 N; 210/602, 615, 617, 620, 221.1, 221.2
See application file for complete search history.

(56) References Cited

U.S. PATENT DOCUMENTS

2003/0201225 A1* 10/2003 Josse .................. C02F 9/00
                                                    210/605
2015/0191382 A1* 7/2015 Blanc ................ C02F 3/085
                                                    210/219
2019/0330090 A1* 10/2019 Zhang ................ C02F 3/34

FOREIGN PATENT DOCUMENTS

| | | |
|---|---|---|
| CN | 203373199 | 1/2014 |
| CN | 103923821 | 7/2014 |
| CN | 104591508 | 5/2015 |
| CN | 204392947 | 6/2015 |
| CN | 204958526 | 1/2016 |
| CN | 107381837 | 11/2017 |
| DE | 3725988 | 2/1989 |
| DE | 19825168 | 10/1998 |
| DE | 19806938 | 8/1999 |
| EP | 3389958 | 10/1990 |
| EP | 0486748 | 5/1992 |
| ES | 2298011 | 5/2008 |
| JP | 2004097093 | 4/2004 |
| JP | 2004099366 | 4/2004 |
| JP | 2017024973 | 2/2017 |
| RU | 2035404 | 5/1995 |
| RU | 2405741 | 12/2010 |
| RU | 2527329 | 4/2014 |
| RU | 147394 | 11/2014 |
| WO | 2010003255 | 1/2010 |
| WO | 2014143359 | 9/2014 |
| WO | 2016050893 | 4/2016 |
| WO | 2017076972 | 5/2017 |

* cited by examiner

BIOREACTOR AND USE THEREOF, METHOD FOR PRODUCING AN ORGANIC NUTRIENT SOLUTION, ORGANIC NUTRIENT SOLUTION, SUBSTRATE MATERIAL AND USE THEREOF FOR CULTIVATING PLANTS

TECHNICAL FIELD

The invention relates to a bioreactor and its use for the conversion of organic residual and/or waste material into an organic nutrient solution with a proportion of at least 10% plant-accessible mineralised nitrogen relative to the total nitrogen content of the nutrient solution, with a reaction tank, where the reaction tank has an input feed, through which suspension can be introduced into the reaction tank, and where the reaction tank has an output feed through which the suspension can be discharged from the reaction tank.

Further, the invention relates to a method for producing an organic nutrient solution containing at least 10% nitrogen accessible to plants.

The invention also relates to a method for producing a substrate material for cultivating plants.

The invention also relates to an organic nutrient solution. In particular, the organic nutrient solution can be an organic plant fertiliser.

The invention also relates to a substrate material for cultivating plants with a biofilm containing ammonifying and/or nitrifying bacteria. The invention also relates to the use of the substrate material for the cultivation of plants.

The invention also relates to the use of ammonifying and/or nitrifying bacteria in the form of a biofilm on a carrier element for the conversion of organic residual and/or waste materials into an organic nutrient solution with a proportion of at least 10% plant-accessible mineralised nitrogen relative to the total nitrogen content of the nutrient solution.

Additionally, the invention relates to a set-up consisting of the bioreactor and an inoculating material designed to inoculate the carrier element and to form a biofilm with ammonifying and/or nitrifying bacteria.

Further, the invention relates to a set-up consisting of a carrier element and an inoculating material designed to inoculate the carrier element and to form a biofilm with ammonifying and/or nitrifying bacteria.

BACKGROUND

Agriculture has always sought out nutrients for farming plants by using and recycling plant and animal residues and waste materials. Organic farming, however, typically follows the rule that nitrogen, in its role as an important plant nutrient, should only be applied in organic form, as organic farm manure/organic commercial fertiliser, for example liquid manure, compost or horn meal. Due to the expansion of the market for organically produced products, the specialisation of farms is increasing and vegetable growers and other farms without livestock are being forced to purchase and use organic commercial fertiliser due to the sale and export of biomass and the lack of appropriate industrial commercial fertiliser. Looking specifically at the rising demand for organic fertilisers, these contain a considerable amount of non-mineralised nitrogen that cannot immediately be absorbed by the plants.

Plant-accessible nitrogen, i.e. nitrogen that can be absorbed directly by plants, is basically understood to take the form of inorganic nitrogen compounds. In contrast, organic nitrogen compounds cannot be directly absorbed by plants. The term "plant-accessible nitrogen" generally refers to nitrogen that is available in the form of ammonium ($NH_4+$) and nitrate ($NO_3$).

Hydroponic, soil-less or soil-poor cultivation systems for plants currently use mineral fertilisers or mineral-organic fertilisers (fertilisers where nitrogen compounds mineralised into organic material from industrial production have been added). Purely organic fertilizer material cannot be used for two reasons. First, the bacterial soil-to-plant interaction in such cultivation systems is either very limited or not applicable in soil-less approaches. Furthermore, a bacterial process that is dependent on external processes—such as nitrification—cannot produce sufficient quantities of mineralised nutrients in the soil which are immediately accessible to plants. Additionally, a controlled, constant and immediate release of nitrogen, which is of particular importance for plants in hydroponic planting systems, cannot be achieved with organic fertilisers.

Another problem is that the conversion of organic fertiliser material, such as compost waste and similar substances, and the release of mineralised nitrogen associated with such substances, depends on a number of environmental factors that are difficult to control, such as soil moisture level, soil temperature and varying concentrations of organic compounds in the soil. This lack of control leads to irregular production and surplus/deficit production of nitrogen in agricultural applications, as well as to economically and environmentally harmful counter-processes, such as denitrification.

Especially for soil-less (or soil-poor) hydroponic/aeroponic cultivation systems, it is essential that the plants are supplied with a nutrient solution that is optimally adjusted, as the lack of a body of soil or the reduced presence of a body of soil does not provide the buffer function needed by the substrate for the supply of nutrients and water. The use of conventional, organic fertiliser material is unsuitable for these systems, as the nitrogen in them is not accessible to plants or is only accessible in insufficient levels. Further, organic fertiliser material cannot be used to achieve a clearly defined and stable nutrient concentration level in the nutrient solution, due to the ongoing nature of decomposition or conversion processes.

In addition to the fundamental disadvantage of organic farming that comes in dispensing with industrially produced mineral nitrogen fertilisers (which would otherwise offer a significant means of increasing yields), the fact that demand for immediately accessible nitrogen for plants—especially in the last third of the growth phase for crops—cannot be provided in time by the use of organic fertilisers previously available on the market, as well as organic fertilisers made from residual and waste materials, continues to be problematic.

SUMMARY

Therefore, the objective at hand is to create a bioreactor, a method and a substrate material with which it is possible to produce a purely organic nutrient solution from organic, residual and/or waste material, where a proportion of plant-accessible nitrogen in the organic nutrient solution is higher than in previously available organic fertilisers.

This object has been resolved by an invention with one or more of the features disclosed herein. In particular, it is proposed that the solution to this objective is found in a bioreactor of the type described in the introduction, where the bioreactor has an aeration device through which oxygen can be introduced into the reaction tank and suspension is carried out in the tank; where at least one carrier element with a settlement surface for the formation of a biofilm made up of microorganisms is arranged inside a receiving chamber in the reaction tank; where the carrier element (again, a minimum of one) can be rinsed and/or flushed with the introduced suspension and the introduce oxygen; and in that the carrier element's surface-to-volume ratio is greater than the surface-to-volume ratio of the receiving chamber. With the use of the bioreactor, it is therefore possible to form a biofilm at the desired point on the settlement surface within the receiving chamber. Ideal growth conditions for ammonifying and/or nitrifying bacteria can therefore be achieved on the settlement surface. As such, the bioreactor provides a more effective carrier element for the conversion reactions intended for the microorganisms, allowing the production of organic nutrient solutions with a higher proportion of nitrogen that is accessible to plants. In particular, it may be preferred that the surface-to-volume ratio of the carrier element is at least eight times greater than the surface-to-volume ratio of the receiving chamber. For example, the aeration unit can be designed so as to introduce oxygen in the form of air.

In line with the results of further development testing, the carrier element (minimum of one) can be made either from one material or from a combination of two or more materials selected from a group of plastics (in particular, food-neutral plastics), minerals (in particular zeolites) and/or a rubber-plastic mixture. It may be particularly useful if the plastic is polypropylene and/or polyethylene and/or rubber, as the microorganisms needed to form the biofilm collect particularly well on these materials. It can also be beneficial for the plastic to be a polyethylene-rubber mixture. It is also possible that a design may use a mineral-plastic mixture and, in particular, a zeolite-plastic mixture.

It can be particularly beneficial for the settlement surface on the carrier element to consist partly of pores and/or recesses. This has the advantage of providing a carrier element with the largest possible collection surface, while ensuring that the carrier element has relatively small outer dimensions. It is preferable for the pores and/or access paths to the recesses to have a diameter of 10 μm to 100 μm, so that the pores and/or access paths allow for the permeation and/or diffusion of both liquids and gasses, as well as for the introduction and establishment of microorganisms. It may be particularly useful if the pores are at least partially or substantially uniform across the surface, i.e. that the material is designed to be particularly porous. Such a design allows for a particularly good flushing and suspension process to be achieved.

Alternatively or in addition to the above, further designs may allow for the carrier element (minimum of one) to be detachable from the reaction tank and, in particular, to be detachable without the use of tools. More specifically, the carrier element can be designed as an interchangeable module. This has the advantage of ensuring that the carrier element can be removed and replaced quickly and easily from the reaction tank. It may also be especially useful if a guide device is designed at the entry of the receiving chamber, through which the carrier element can be fed into the receiving chamber by being pushed or inserted. A guiding device can therefore help to determine the final position of the carrier element in the receiving chamber.

In order to facilitate the introduction of oxygen into the reaction tank and to more effectively prevent anaerobic reactions, the invention may be so designed that oxygen is introduced into the reaction tank and/or into the carrier element (minimum of one) through the use of the aeration device via a gas input feed. In such a connection, it may be advantageous for the aeration device to have at least one compressor or a gas connector which could allow for the introduction of gas to be regulated more effectively. It is preferable for the gas input feed to be independent of the input feed and the output feed, so that oxygen and suspension can be introduced to the system independently of one another. This may, for example, also allow for the oxygen to be introduced in the form of air. One advantage of this is that the system would not require the input of pure oxygen, but rather could use circulating air, which is available in unlimited quantities.

Alternatively or in addition to the above, the aeration device, and in particular one or another of the above-mentioned aeration devices may take the form of an aeration plate with a number of aeration openings that are formed on the floor of the reaction tank. In particular, the aeration device can be used to produce a uniform gas bubble density within the reaction tank, preferably inside the receiving chamber, so that the system can ensure as uniform an aeration process as possible within the reaction tank. It is similarly preferable for the aeration device to be conical in shape, so that it is easier to prevent the aeration openings from becoming clogged with solid particles falling through with the suspension.

In order to achieve a particularly efficient circulation of the suspension inside the receiving chamber, the bioreactor can be fitted with a pumping device. The pumping device can be designed as a centrifugal pump or a circulation pump, for example. It may also be advantageous if the pumping device is used to pump the suspension through the input feed into the reaction tank and through the output feed from the reaction tank. In order to set different flow rates through the reaction tank and/or the input and output feeds, the pumping capacity of the pumping device can be adjustable, i.e. more specifically it could be either manually adjustable and/or programmable. It is preferable for a suspension flow direction within the reaction tank to be generated by the pumping device and to run at least partially in the opposite direction and/or at least partially in the direction of the oxygen flow. In this way, it is possible to achieve a particularly effective mixing of the suspension with the oxygen. In order to automate the execution of a production method comprising several steps within a bioreactor, it is preferable for the pumping device to be programmed in such a way that its programme includes a number of incremental steps that can be set to run automatically.

In order to create ideal growth and/or conversion conditions for the microorganisms, the bioreactor can be fitted with a heating device, through which the receiving chamber in the reaction tank and/or the suspension contained in the receiving chamber of the reaction tank can be heated to an adjustable temperature. In particular, a temperature of 20° C. to 34° C., and preferably a temperature of 22° C. to 32° C.

So that the carrier element can be removed easily from the bioreactor, the invention can be so designed as to provide—as shown through further development testing—an opening in the reaction tank, and to include a sealing unit in the bioreactor which can be used to close the opening of the reaction tank. It is preferable for this sealing unit to be able to provide a seal for the opening of the reaction tank that is liquid-tight and/or to be pressure-resistant.

In order to avoid disruptive external influences on the conversion of the organic residual and/or waste material into the organic nutrient solution, a wall of the reaction tank and one or another of the sealing units described above can be designed to be opaque. This allows for the conversion rate to be improved.

It can also be useful for the settlement surface to be hydrophobic.

In order to provide an environment in which it is easier for the microorganisms to adhere to the settlement surface, the settlement surface can be more coarse or rough in texture than the inside of the reaction tank wall.

In order to provide the largest possible total areas for the microorganisms to collect, the bioreactor can be fitted with several carrier elements. Here, it is preferable for the carrier elements to be designed and/or arranged so that they can move relative to one another. It is preferable for the carrier elements to be loosely arranged within the receiving chamber. By circulating the suspension, the carrier elements can therefore also be circulated and/or moved in the resulting flow. This helps to improve gas and suspension exchange in the carrier elements.

In line with particularly preferable further development testing, a large number of chips—and in particular a large number of plastic flow chips—can be used as carrier elements, with the chips arranged in no particular order or sequence inside the reaction tank. In such cases, the disordered arrangement of the chips can allow for the chips to become tangled. It is therefore preferable to ensure that the settlement surfaces of the chips are designed so that they do not adhere to one another and/or are not rinsed with oxygen to such an extent that unwanted denitrification processes can take place. It is especially preferable for the chips to be designed as a spiral and/or wavy shape chips, or as a combination of several shape chips. This is a particularly good way to prevent the settlement surfaces on the chips from adhering too or lying against one another.

It is preferable for each of the chips to have a length of between 2 cm and 10 cm and/or a width of 0.5 cm to 1.5 cm and/or a depth of 50 μm to 500 μm.

Alternatively or in addition to the above, at least one porous tube can be included as a carrier element. In particular, the tube can be positioned transversely or parallel to the flow direction of the oxygen introduced into the reaction tank and/or arranged transversely or parallel to the flow direction of the suspension introduced into the reaction tank. As such, it is possible to achieve a particularly good flow in the area around the tube.

In line with the results of further development testing, the design can allow for oxygen to be introduced via a gas input feed through the porous tube mentioned above or another porous tube. In particular, this gas input supply can be designed as a bypass gas line branching off from a main gas line, preferably to a main gas line which then leads to an aeration device or devices as mentioned above. This would enable a particularly good supply of oxygen to the microorganisms settled on the inner side of the porous tube wall. Here, it is preferable for the bioreactors to be fitted with several carrier elements designed as porous tubes. Such a design may also allow for the tubes to be integrated into a gas line running inside the receiving chamber. This gas line can be connected to the input feed and/or the output feed. It is preferable for a shut-off valve to be inserted into the gas line inside the receiving chamber before and/or after the tube. In this way, it is possible to increase the internal pressure within the tube easily by closing the shut-off valve placed downstream of the tube in the direction of flow, allowing for the flow of suspension to be directed through the pores in the tube wall—at least for a short time. Similarly, it is possible to prevent the introduction of suspension into the tube by closing a shut-off valve arranged upstream of the tube in the direction of flow.

In line with the results of further development testing, the system can be designed so that the carrier element is designed as zeolite granulate. In particular, the zeolite granulate can have a grain size of 0.6 mm to 1.0 mm. Here, it is preferable for the zeolite granulate and/or another carrier material to be arranged inside the reaction tank, ideally as a textile bag. This prevents the carrier material from being washed into areas in the receiving chamber which are difficult to aerate and/or mix.

Alternatively or in addition to the above, a further aeration device can be arranged connected to the collection unit mentioned above, as well as at the base of such a unit, or another such unit. Through this unit, oxygen could be introduced into the zeolite granulate and/or another carrier element. Here, it is preferable for the further aeration device to be connected to a bypass gas line branching off from a main gas line. The further aeration device then allows for a particularly good circulation of oxygen around the zeolite granulate and/or another carrier element.

In order to better prevent solids in the suspension from settling on the floor of the receiving chamber, the input feed can open into the reaction tank above and/or at the same level as the output feed. This means that sinking particles can be introduced further up into the receiving chamber and discharged further down from the receiving chamber. Alternatively or in addition to the above, the bioreactor can be fitted with several input feeds and/or several output feeds. Here, it is preferable if the function of the input feed or the output feed within the bioreactor can be determined by an adjustable suspension flow direction during use. This would make it possible to set up at least two different flow directions within the reaction tank—preferably simultaneously—with their use as either input or output feeds dependant on the flow direction. In this way, at least two output feeds can lead out of the reaction tank near the flow in order to discharge settled particles and suspension even more efficiently.

In order to achieve particularly good circulation of the suspension within the receiving chamber of the reaction tank, at least two suspension flow directions within the reaction tank and/or within the feeds of the bioreactor can be set through the use of the pumping device mentioned above or another such device. In order to achieve particularly good circulation, the input feed and the output feed any alternatively or additionally can be separated from each other by means of a pumping device or the pumping device already mentioned above. In particular, the bioreactor may have a suspension circuit comprising the input feed, the output feed, the pumping device and the reaction tank, so that the suspension can be passed several times pas the biofilm within the reaction tank.

To provide easier control of the suspension flow, a shut-off valve can be positioned in the input feed between the reaction tank and one of the pumping devices or the sole pumping device and/or a shut-off valve position in the output feed between the reaction tank and the pumping device or one of the pumping devices.

In line with the results of further development testing of the bioreactor, a bypass gas line can branch off from the input feed, especially after the pumping device (or one of the pumping devices) and/or before the shut-off valve (or one of the shut-off valves), which opens into the reaction tank. As such, suspension can also be introduced into the reaction tank via the bypass gas line. Here, it is preferable for the bypass gas line to be fitted with a shut-off valve. It may also be preferable for the bypass gas line to be used as a drain in the event of a change—and in particular a reversal—of the direction of suspension flow through the pumping device. This allows for the variability of the flow paths to be increased, leading to a more effective circulation of the suspension in the reaction tank.

It may be particularly beneficial for a biofilm containing ammonifying and/or nitrifying bacteria to be present on the settlement surface. The design could provide, for example, for a proportion of ammonifying and/or nitrifying bacteria on the biofilm that is set to one of the following levels: at least 2%; preferably at least 4%; preferably at least 6%; preferably at least 10%; preferably at least 15%; preferably at least 20%; preferably at least 25%; preferably at least 30%; preferably at least 40%; preferably at least 50%; preferably at least 60%; preferably at least 70%; preferably at least 80%; preferably at least 90%; preferably approximately 100%.

In order to produce the largest possible surface area for the microorganisms to settle, the carrier element (minimum of one) can feature a number of settlement surfaces, where the settlement surfaces are designed to be curved in such a way that sticking and/or contact between the settlement surfaces of a carrier element and/or sticking and/or contact between the settlement surfaces of a different carrier element can be avoided.

The task set out above is also resolved by the invention through the features of an independent method claim for the production of an organic nutrient solution. More specifically, the method for the production of an organic nutrient solution is proposed here as a means of resolving the task set out above, namely in providing for an organic nutrient solution with a proportion of at least 10%—and in particular at least 25%, preferably at least 50%, and more preferably still, at least 75%—of mineralised nitrogen that is accessible to plants, based on the total nitrogen content of the organic nutrient solution. Here, it is preferable for the proportion of nitrate in the plant-accessible mineralised nitrogen to be higher than the ammonium portion. It may be particularly beneficial for there to be a $NO_3:NH_4^+$ ratio of at least 2:1—in particular at least 10:1, preferably at least 25:1, and more preferably still, at least 50:1—in the organic nutrient solution. The method consists of the following steps:

an inoculation step, inoculating a carrier element, preferably a carrier element in the bioreactor as described and claimed in this text, with an inoculation material containing ammonifying and/or nitrifying bacteria, formation of a biofilm with ammonifying and/or nitrifying bacteria on the carrier element, an incubation step, incubating an organic residual and/or waste material within the biofilm—in particular in a reaction tank—where the ammonifying and/or nitrifying bacteria convert organically bound nitrogen in the residual and/or waste material into mineralised nitrogen.

For the first time in the development of such devices, this method makes it possible to produce an organic nutrient solution from organic residual and/or waste materials that can be used as plant fertiliser, in which the proportion of nitrogen accessible to plants has been dramatically increased as a result of the specialised method. In line with a preferred design, it is possible to achieve a clear shift in the ratio of the nitrate to ammonium content of the nitrogen accessible to plants. Especially in soil-less, hydroponic systems, plants are mainly dependent on nitrate, because it is better absorbed. Additionally, it is also possible to significantly reduce the odour pollution that often occurs with organic residual and/or waste materials and which is caused in particular by ammonium, even achieving complete odour neutralisation in the final organic nutrient solution.

The task set out above is resolved, in line with the invention, through the features of the independent method claim for the production of a substrate material for the cultivation of plants. More specifically, a method for the production of a substrate material for the cultivation of plants is proposed here as a means of resolving the aforementioned task and comprises the following steps:

an inoculation step, inoculating a carrier element—preferably a carrier element in a bioreactor in line with the above claims—with an inoculation material containing ammonifying and/or nitrifying bacteria, formation of a biofilm with ammonifying and/or nitrifying bacteria on the carrier element.

Through the method described above, it is possible to inoculate carrier elements with ammonifying and/or nitrifying bacteria and to grow a biofilm on the carrier element. The carrier element can then be used, for example, in a bioreactor, as described and claimed in this text, or as a substrate material, also as described and claimed in this text.

The following further development testing phases refer to both of the methods described above.

In order to achieve particularly effective inoculation and/or conversion, the inoculation material and/or the organic residual and/or waste material can be used in liquid form. Here, it is preferable for the inoculation material and/or the organic residual and/or waste material can be used in a suspension form. This allows for particularly good saturation of the carrier element with the inoculant and/or the organic residual and/or waste material. Further, especially simple and effective circulation of the organic residual and/or waste material is possible. To this end, a solid inoculation material and/or organic residual and/or waste material can be mixed with water to produce the suspension.

It can be advantageous to use the inoculation material or a combination of one or more inoculation materials selected from a group consisting of compost (in particular, bark compost), worm excrement (in particular earthworm excrement), soil (in particular, field soil). In addition to ammonifying and/or nitrifying bacteria, these inoculation materials contain mucilage and/or proteins which accelerate the formation of the biofilm on the carrier element and stabilise the biofilm. In principle, excrement from worms living in the soil is suitable, as they are rich ammonifying and/or nitrifying bacteria.

In one particularly advantageous design, the proportion of organic material in the organic residual and/or waste material can range from 5% or 60%.

Alternatively or in addition to the above, a carbon/nitrogen ratio in the residual and/or waste organic material can be 11 or less. Values above 11 will reduce the conversion rates.

Further, it can be advantageous for a total nitrogen content in relation to the total mass of the organic residual and/or waste material to be at least 0.3%.

It can also be ensured that a proportion of nitrate-bound nitrogen relative to the total content of plant-accessible nitrogen in the organic residual and/or waste material is less than a proportion of ammonium-bound nitrogen. This ration can be adjusted through the process so that nitrate is present in the majority of cases, rather than ammonium.

In order to create ideal growth conditions for the ammonifying and/or nitrifying bacteria, some or all of the process steps can be carried out at a temperature of 20° C. to 34° C., preferably 22° C. to 32° C., and especially at a constant temperature.

In order to prevent unwanted denitrification processes through anaerobic denitrifying bacteria and to supply aerobic ammonifying and/or nitrifying bacteria with sufficient oxygen, oxygen can be introduced into the reaction tank and/or into the carrier element while carrying out some of the steps.

In order to better prevent anaerobic bacteria from settling during the inoculation step, the inoculation material can be circulated during the inoculation step. More specifically, by pumping the inoculation material several times and/or in different flow directions through a—preferably closed—circuit, in which the carrier element is placed. In particular, inoculation material and parts of the biofilm which are stuck to the carrier element as a result of the circulation process can be removed and attached elsewhere. This removal and reattachment process promotes bacteria growth.

Alternatively or in addition to the above, the residual and/or waste organic material can be circulated during the incubation step to better prevent sedimentation of solids and the occurrence of anaerobic degradation processes. More specifically, the organic residual and/or waste material can be pumped several times and/or in different flow directions through a—preferably closed—circuit, in which the carrier element is placed.

In order to further optimise the conversion efficiency of the bacteria, the inoculation step can be divided into an initial phase with continuous aeration and/or recirculation, and a second phase with discontinuous aeration and/or recirculation. Here, it is preferable for pauses in the aeration and/or circulation processes, more specifically, pauses of 30 to 50 minutes per hour, during this second phase.

It can also be beneficial for the inoculation and incubation steps to be performed in different reaction tanks. Here, it is preferable for the reaction tank used during the inoculation step to have a smaller volume capacity than the reaction tank used during the incubation step.

It is also possible to ensure that the incubation step comprises an ammonification step and/or a nitrification step, where organically bound nitrogen is converted during the ammonification step into ammonium from the organic residual and/or waste material by the ammonifying bacteria in the biofilm and/or where ammonium is converted into nitrate during the nitrification step by the nitrifying bacteria in the biofilm. Depending on which organic residual and/or waste material is used and what initial proportions of nitrogen accessible to plants is contained in that material, it is occasionally possible that only the nitrification step is required. In particular, the incubation step can be carried until the organic nutrient solution has reached a point where it contains more nitrate than ammonium, preferable until a NO3:NH4+ ratio of at least 2:1, in particular at least 3:1, preferably at least 10:1, preferably 25:1, and more preferably still at least 50:1. In order to determine what proportion of plant-accessible nitrogen is present, a measuring step can be carried out at regular intervals or continuously. Such measuring methods known to experts in the field can be used to determine the nitrate and/or ammonium concentration and/or a total nitrogen concentration.

In line with further development testing, at least one porous tube—in particular a porous rubber-plastic tube—can be used as a carrier element, where oxygen and inoculation material and/or oxygen and residual and/or waste material are introduced into the tube at separate points. Here, it is preferably for the internal pressure in the tube to be adjusted during the inoculation step and/or during the incubation step, in particular by increasing a flow of inoculation material and/or residual and/or waste material through the tube for a specific period of time and/or by increasing a volume flow of oxygen through the tube for a specific period of time. The porous tubular shape of the carrier element has the advantage of a relatively large surface area on which the microorganisms can settle. Especially with an open-pored design, suspension pressed through the tube can also escape through pores that penetrate through the tube wall. As such, this offers, firstly, especially efficient inoculation of the settlement surfaces and, secondly, particularly effective oxygen and nutrient supply for the bacteria in the biofilm. More specifically, the tube can be designed to be adjustable, i.e. expandable, which has the advantage of offering pore diameters that can expand should the pressure inside the tube increase. Therefore, it is possible to achieve an increased flow rate through the pores, for example to ensure better circulation of suspension within the tube.

In order to achieve particular effective saturation of the carrier material, the carrier element can be completely immersed in the inoculation material during the inoculation step and/or the carrier element can be completely immersed in the residual and/or waste material during the incubation step.

Further, the invention also relates to an organic nutrient solution—in particular an organic plant fertiliser—produced by the method described above and claimed in this text and/or in a bioreactor of the type described above and claimed in this text, with a proportion of at least 10%—in particular at least 25%, preferably at least 50% and more preferably still at least 75%—of plant-accessible mineralised nitrogen relative to the total nitrogen content of the organic nutrient solution. Here, it is preferable for the nitrate proportion of the plant-accessible mineralised nitrogen to be higher than the portion of ammonium. Further, it is preferable for the organic nutrient solution to have a NO3:NH4+ ratio of at least 2:1—in particular at least 10:1, preferably at least 50:1. The organic nutrient solution has the advantage of also being used in organic farming, unlike industrially produced mineral fertilisers. Organic plant fertilisers produced purely from organic residual and/or waste material with such a high nitrogen mineralisation rate are not currently known.

Here, it is preferable for the organic nutrient solution to be a liquid fertiliser.

In order for the organic nutrient solution to be used in organic farming, it is necessary for the mineralised nitrogen accessible to plants to be converted exclusively or predominantly from organically bound nitrogen and/or for the organic nutrient solution to be free from industrially produced mineral fertiliser. Industrially produced mineral fertilisers include, for example, mineral salts obtained through chemical or physical processing from raw materials that have been mined primarily in industrial mining processes, especially nitrogen fertilisers that are not of organic origin. The organic residual and/or waste material used as a starting material for the production of the organic nutrient solution can comprise, for example, plant and/or animal waste, fermentation residues, especially from biogas plants, liquid manure, slurry, manure from livestock, organic secondary raw materials from the food, luxury food and animal feed industries.

The invention further related to a substrate material for the cultivation of plants that uses a biofilm with ammonifying and/or nitrifying bacteria produced through the method described above and claimed in this text and/or through the use of a bioreactor as described above and claimed in this text. It is preferable for the carrier element to have pores and/or recesses with a diameter of 10 μm to 100 μm.

In line with further development testing of the substrate material, the carrier element can be designed as a porous tube. It is preferable for the carrier element to be designed as a porous tube made of a plastic-rubber mixture. Here, it is worthwhile referring to the design options given for the carrier element of the bioreactor above, which can also be used for the substrate material.

In line with further development testing of the substrate material, the carrier element can be made of a mineral, especially zeolites. In particular, the carrier element can be designed from zeolite granulate. Zeolite is particularly well-suited as a soil additive, as its porous composition gives it a particularly large surface area on both its inner and outer surfaces, which can act as settlement surfaces. As such, despite the relatively large settlement surface, the zeolite nonetheless occupies a relatively small space.

In order to better protect plants cultivated in contact with or near to the substrate material from shortages of nutrients and/or water, the carrier element can be designed to have a sponge effect, through which the substrate material can store liquids. This effect can be achieved, for example, through the use of a carrier element that is made at least in part from foam material and from foam plastic in p articular.

The invention further relates to the use of ammonifying and/or nitrifying bacteria in the form of a biofilm in a carrier element, and in particular in a bioreactor as described above and claimed in this text, for the conversion of organic residual and/or waste materials into an organic nutrient solution with a proportion of at least 10%—in particular at least 25%, preferably at least 50%, and more preferably still at least 75%—of plant-accessible mineralised nitrogen relative to the total nitrogen content of the nutrient solution, in particular by following the steps in the method described above and claimed in this text. Here, it is preferable for a $NO_3:NH_4+$ ratio of at least 2:1—in particular at least 3:1, in particular at least 10:1, preferable at least 25:1, and more preferably still at least 50:1—is present in the final organic nutrient solution.

The invention also relates to the use of the organic nutrient solution, as described above and claimed in this text, for the fertilisation of plants, and in particular for the fertilisation of plants grown according to the criteria requires for organic agriculture. The organic nutrient solution is more efficient than conventional organic plant fertilisers in compensating for soil leaching, which occurs in particular in the last third of the growth period for crops.

Following one particularly advantageous design, the organic nutrient solution can be used in hydroponic cultivation systems especially in soil-less and/or low-soil hydroponic cultivation systems. In contrast to other purely organic plant fertilisers, the organic nutrient solution is also suitable for use in soil-less and/or low-soil cultivation systems, as the proportion of plant-accessible nitrogen—especially plant-accessible nitrate—is significantly higher than with conventional organic plant fertilisers.

The invention further relates to the use of the substrate material—as described above and claimed in this text—for the cultivation of plants. The use is especially designed for the cultivation of agricultural plants. Here, it is preferable for the substrate material to be mixed with a plant soil, especially as a soil additive. In particular, it can be mixed through an arable soil taken from fields. In this way, it is possible to accelerate the transformation processes involved in ammonification and/or nitrification that occur naturally in the soil. As such, organically bound nitrogen in the soil can be converted into nitrogen that is accessible to plants at a faster rate. This additionally means that the fertility of natural soils and their respective crop yields can be increased.

Alternatively or in addition to the above, it is also possible that the substrate material can be used as an anchoring material, especially in hydroponic cultivation systems. The substrate material can therefore be used to allow plants to maintain access to the beneficial material when the soil otherwise used for this purpose is not available or not available in sufficient quantities.

In line with further development testing, the plants can be positioned so that they are at least partially in direct contact with an outer surface of the substrate material's carrier element through their roots. In particular, an organic nutrient solution—especially as described above and claimed in this text—can be passed through the carrier element. Here, it is preferable for the organic nutrient solution to be diffused and/or pressed through the pores in a carrier element wall, from the inner side of the carrier element, through to the outer side of the carrier element. This enables particularly effective nutrient supply to the plants. In one example, it is possible to position the carrier element in an arable soil. Further, the carrier element can also be used in this form—as mentioned above—in a system without soil or very little soil.

In line with particularly preferable further development testing, the plants can be positioned so that they are at least partially in direct contact with an outer surface of the substrate material's carrier element through their roots; where an organic residual and/or waste material is passed through the carrier element; where organically bound nitrogen in the residual and/or waste material is converted into mineralised nitrogen by the bacteria in the biofilm; where the mineralised nitrogen is diffused and/or pressed through pores in a carrier element wall from the inner side of the carrier element through to the outer side of the carrier element; and where the roots of the plants—which are at least partially in contact with the outer side of the carrier element—absorb mineralised nitrogen accessible to plants. In this way, the organic residual and/or waste material can be used directly for supply to the plants without the need for a separate conversion process involving the organic nutrient solution. Here, it is surprising that results show that the plants receive a sufficient supply of nitrogen through the efficient conversion of organically bound nitrogen into plant-accessible nitrogen using the biofilm in the carrier element.

The invention further relates to a set-up comprising a bioreactor—as described above and claimed in this text—and an inoculating material for inoculating the carrier element and forming a biofilm with ammonifying and/or nitrifying bacteria.

The invention further relates to a set-up consisting of a carrier element and an inoculating material, used to inoculate the carrier element and to form a biofilm with ammonifying and/or nitrifying bacterial, in particular for carrying out the method described above and claimed in this text and/or in a bioreactor described above and claimed in this text and/or for the use described above and claimed in this text.

Below, the invention will be explained in greater detail through a number of design examples, however it is not limited to these design examples. Further examples of potential design possibilities can be derived from the features of individual or multiple claims in combination with one another and/or from individual or multiple features taken from the various design examples.

DESIGN EXAMPLES

Example 1

In the following examples, a bioreactor is used to carry out the method of producing an organic nutrient solution, as described and claimed in this text.

First, fermentation residues with a small portion of plant-accessible nitrogen (1%) are added to the receiving chamber in the reaction tank—these fermentation residues are obtained from the fermentation of biowaste comprised of waste collected from private households (92%); vegetable matter from the production of food, beverages and animal feed; vegetable matter from gardening, landscaping and forestry; and fat and fat residues.

Alternatively or in addition to the above, fermented sugar beet molasses (vinasse) may be added as a residue from the food and feed industry with a nitrogen content of less than 0.5%.

The inoculation of the carrier elements then takes place in the first tank, as explained above.

The inoculated plastic substrate—in chip form, weighting 200 g and with an estimated plastic contact area of 1.76 m$^2$—is then added to a second tank and topped up with 720 ml of organic liquid fermentation residue and 111 water.

The fermentation residue thus has the following composition:
- 0.46% N total nitrogen
- 0.18% N ammonium nitrogen
- 0.12% $P_2O_5$ total phosphate
- 0.42% K2O total potassium oxide
- 0.0029% Zn total zinc
- Secondary components:
- 0.11% MgO total magnesium oxide
- 0.04% S Sulphur
- 0.66% CaO basic active ingredients
- 6.41% organic substance
- Bulk density 1040 kg/m$^3$
- pH value 8.4

As such, the total nitrogen contained in the initial solution is calculated at 294 mg/l. The fermentation residue material introduced together with the 11 l water produces the following initial values (as measured with MQuant™ test strips from Fa. Merck KgaA, 64271 Darmstadt, Germany):
- pH=7.4
- NH$_4$=200 mg/l corresponding to NH4-N=155 mg/l
- NO$_3$=0 mg/l During the incubation step, the liquid is tempered to 25° C. and air is injected into the solution for 6 minutes per hour over 14 hours per day. This corresponds to a total air volume of 25.2 m$^3$ per day.

After 5 days, the NO3 value will have reached 250 mg/l (corresponding to 56 mg/l NO$_3$—N) and the NH4 value will have dropped 90 mg/l (corresponding to 70 mg/l NH$_4$—N). After 9 days the NO$_3$ will reach its maximum of 1000 mg/l (226 mg/l NO$_3$—N) and the NH$_4$ value will be 15 mg/l (12 mg/l NH$_4$—N). At this point, 81% (238 mg/l) of the total nitrogen contained in the initial solution will have been converted to plant-accessible form. The nitrogen will be present at a NO$_3$ to NH$_4$ ratio of 50:1. In the initial solution, 39% of the total nitrogen is present as 100% NH$_4$ that is directly accessible to plants.

In Central Europe, the average annual rate of mineralisation in the soil is about 1-2% organic nitrogen depending on temperature and soil moisture. At a mineralisation rate of 2%, the calculated total nitrogen of 294 mg/l in the soil would mineralise at a rate of 5.88 mg/l per year. After 9 days, 0.145 mg/l would be mineralised. As such, this method results in a mineralisation rate that is more than 1500 times higher compared to soil mineralisation.

Example 2

In this case, vinasse is used as the organic residual and/or waste material.

The inoculated plastic carrier material—in chip form, weighting 150 g and with an estimated plastic contact area of 1.32 m$^2$—is added to the second tank and the tank is filled with 60 ml vinasse and 93 l water.

The composition of the vinasse is as follows:
- 4.5% N total nitrogen
- 0.5% N available nitrogen
- 6% $K_2O$ total potassium oxide
- Secondary components:
- 1.5% S water-soluble sulphur
- 2.5% Na water-soluble sodium
- 48% organic substance
- Density 1360 kg/m$^3$ As such, the resulting total nitrogen is 40 mg/l. The vinasse combined with 93 l water produces the following initial values (as measured with MQuant™ test strips from Fa. Merck KgaA, 64271 Darmstadt, Germany):
- pH=6.8
- NH4=20 mg/l corresponding to NH4—N=16 mg/l
- NO3=5 mg/l corresponding to NO3-N=1.2 mg/l During the incubation step, the liquid is tempered to 25° C. and air is injected for 10 minutes per hour and for 14 hours a day. This corresponds to a total air volume of 42 m$^3$ per day.

After 5 days, the NH$_4$ value will have reached 45 mg/l (corresponding to 35 mg/l NH$_4$—N) and after 9 it will have reached a maximum value of 80 mg/l (corresponding to 62 mg/l NH$_4$—N). After 9 days, the NO$_3$-Wert will sit at 3 mg/l and rises to a maximum value of 240 mg/l (50 mg/l NO$_3$—N) by day 11. At this point, the NH$_4$ value will be 8 mg/l (6 mg/l NH$_4$—N).

At this point, 140%* (56 mg/l) of the total nitrogen contained in the initial solution will be available in plant-accessible form. The nitrogen is present in a NO$_3$ to NH$_4$ ratio of 8:1. In the initial solution, 11% of the total nitrogen is directly available to the plants, with a NO$_3$ to NH$_4$ ratio of 1:10.

In Central Europe, the average annual rate of mineralisation in the soil is about 1-2% organic nitrogen depending on temperature and soil moisture. At a mineralisation rate of 2%, the calculated total nitrogen of 40 mg/l in the soil would mineralise at a rate of 0.8 mg/l per year. After 9 days, 0.02 mg/l would be mineralised. As such, this method results in a mineralisation rate that is more than 2500 times higher compared to soil mineralisation.

The total nitrogen level is determined according to the Kjeldahl method. However, here, a substantive value for nitrogen contained in the protein fraction is determined in part by not recording the fluctuations of nitrogen fraction levels during its function in the amino acid composition process. As a result, the true nitrogen content in the starting material is higher than the value typically determined by Kjerdahl analysis.

Example 3

Here, a porous tube is used as the carrier material.

In this example, the inoculated carrier element—here in tubular form—guides the fermentation residues. The fermentation residues, with a low percentage of accessible nitrogen (less than 1%) are obtained from the fermentation of biowaste comprised of waste collected from private households (92%); vegetable matter from the production of food, beverages and animal feed; vegetable matter from gardening, landscaping and forestry; and fat and fat residues.

Alternatively or in addition to the above, sugar beet molasses (vinasse)-fermented in the tubular inoculated carrier element—can be combined with the above materials as a residual material of the food and feed industry, with an available nitrogen content of less than 0.5%.

A nutrient solution with nitrogen that is immediately accessible to plants emerges through the pores of the carrier element, which is then absorbed by the plant roots which are in contact with the substrate as a plant-accessible, mineral nutrient solution.

To this end, 720 ml of organic liquid fermentation residue and 13 l of water are added.

The fermentation residue thus has the following composition:

0.46% N total nitrogen
0.18% N ammonium nitrogen
0.12% $P_2O_5$ total phosphate
0.42% K2O total potassium oxide
0.0029% Zn total zinc
Secondary components:
0.11% MgO total magnesium oxide
0.04% S sulphur
0.66% CaO basic active ingredients
6.41% organic substance
Bulk density 1040 kg/m3
pH value 8.4

As such, the resulting total nitrogen is 251 mg/l. The fermentation residue material introduced during this method results in the following initial values (as measured with MQuant™ test strips from Fa. Merck KgaA, 64271 Darmstadt, Germany):

pH=7.2
NH4=180 mg/l corresponding to 140 mg/l $NH_4$—N
NO3=0 mg/l

Measuring the drained, collected liquid (A) and on the outer surface of the inoculated tubular carrier element (B), the following are reached after 3 days:

|   | NO3 (NO3—N) mg/l | NH4 (NH4—N) mg/l | NO3 to NH4 ratio |
|---|---|---|---|
| A | 40 (9) | 190 (148) | 1:4.75 |
| B | 300 (69) | 50 (34) | 6:1 |

And after 5 days:

|   | NO3 (NO3—N) mg/l | NH4 (NH4—N) mg/l | NO3 to NH4 ratio |
|---|---|---|---|
| A | 50 (11) | 180 (140) | 1:3.6 |
| B | 500 (113) | 80 (62) | 6.25:1 |

With an uninoculated tubular carrier element, supplied in parallel with the initial solution, the initial values for A and B are recorded unchanged after both 3 and 5 days.

Example 4

Here, 25 ml of organic vinasse and 10 l of water are added through the use of the inoculated tubular carrier element.

The composition of the vinasse is as follows:
4.5% N total nitrogen
0.5% N available nitrogen
6% $K_2O$ total potassium oxide
Secondary components:
1.5% S water-soluble sulphur
2.5% Na water-soluble sodium
48% organic substance
Density 1360 kg/m³

As such, the resulting total nitrogen in the initial solution is 153 mg/l. The vinasse—combined with 10 l water—results in the following initial values (as measured with Mquant test strips from Fa. Merck KgaA, 64271 Darmstadt, Germany):

pH=6.5
NH4=15 mg/l corresponding to 12 mg/l $NH_4$—N
NO3=0 mg/l

Measuring the drained, collected liquid (A) and on the outer surface of the inoculated tubular carrier element (B), the following are reached after 1 day:

|   | NO3 (NO3—N) mg/l | NH4 (NH4—N) mg/l | NO3 to NH4 ratio |
|---|---|---|---|
| A | 35 (27) | 5 (4) | 7:1 |
| B | 35 (27) | 5 (4) | 7:1 |

After 7 days:

|   | NO3 (NO3—N) mg/l | NH4 (NH4—N) mg/l | NO3 to NH4 ratio |
|---|---|---|---|
| A | 5 (1) | 80 (62) | 1:16 |
| B | 90 (21) | 8 (6) | 11:1 |

After 14 days:

|   | $NO_3$ ($NO_3$—N) mg/l | $NH_4$ ($NH_4$—N) mg/l | $NO_3$ to $NH_4$ ratio |
|---|---|---|---|
| A | 20 (5) | 150 (117) | 1:7.5 |
| B | 400 (92) | 70 (55) | 5.7:1 |

With an uninoculated tubular carrier element, supplied in parallel with the initial solution, the initial values for A and B are recorded unchanged after 1, 7 and 14 days.

Example 5

Here, zeolite granulate is used as the carrier element.

The inoculated zeolite granulate is mixed into a planting soil. Fermentation residues with a small amount of accessible nitrogen (less than 1%) are added to the zeolite soil mixture—these fermentation residues are obtained from the fermentation of biowaste comprised of waste collected from private households (92%); vegetable matter from the production of food, beverages and animal feed; vegetable matter from gardening, landscaping and forestry; and fat and fat residues.

Alternatively or in addition to the above, fermented sugar beet molasses (vinasse) can be added to the zeolite soil mixture as a residual material from the food and feed industry, with an accessible nitrogen content of less than 0.5%.

The inoculated zeolite granulate—weighing 400 g and having an estimated contact area of 21.6 m$^2$—are added to the second tank and topped up with 440 ml of the organic liquid fermentation residue and 28 l water.

The fermentation residue thus has the following composition:
- 0.46% N total nitrogen
- 0.18% N ammonium nitrogen
- 0.12% $P_2O_5$ total phosphate
- 0.42% $K_2O$ total potassium oxide
- 0.0029% Zn total zinc Secondary components:
- 0.11% MgO total magnesium oxide
- 0.04% S sulphur
- 0.66% CaO basic active ingredients
- 6.41% organic substance
- Bulk density 1040 kg/m$^3$
- pH value 8.4

As such, the resulting total nitrogen in the initial solution is 74 mg/l. The fermentation residue material—combined with 28 l water—results in the following initial values (as measured with Mquant test strips from Fa. Merck KgaA, 64271 Darmstadt, Germany):
- pH=7.4
- $NH_4$=80 mg/l corresponding to 56 mg/l $NH_4$—N
- $NO_3$=5 mg/l corresponding to 1 mg/l $NO_3$—N After 5 days, the $NO_3$ value will have reached 75 mg/l (corresponding to 17 mg/l $NO_3$—N) and the $NH_4$ value will have fallen to 5 mg/l (corresponding to 4 mg/l $NH_4$—N). At this point, 28% (21 mg/l) of the total nitrogen contained in the initial solution will have become available in plant-accessible form. The nitrogen is present in a $NO_3$ to $NH_4$ ratio of 15:1. In the initial solution, 77% of the total nitrogen is present in a $NO_3$ to $NH_4$ ratio of 1:16.

BRIEF DESCRIPTION OF THE DRAWINGS

Below, the bioreactor is described in greater detail through several figures.

They show.

DETAILED DESCRIPTION

Figure 1:
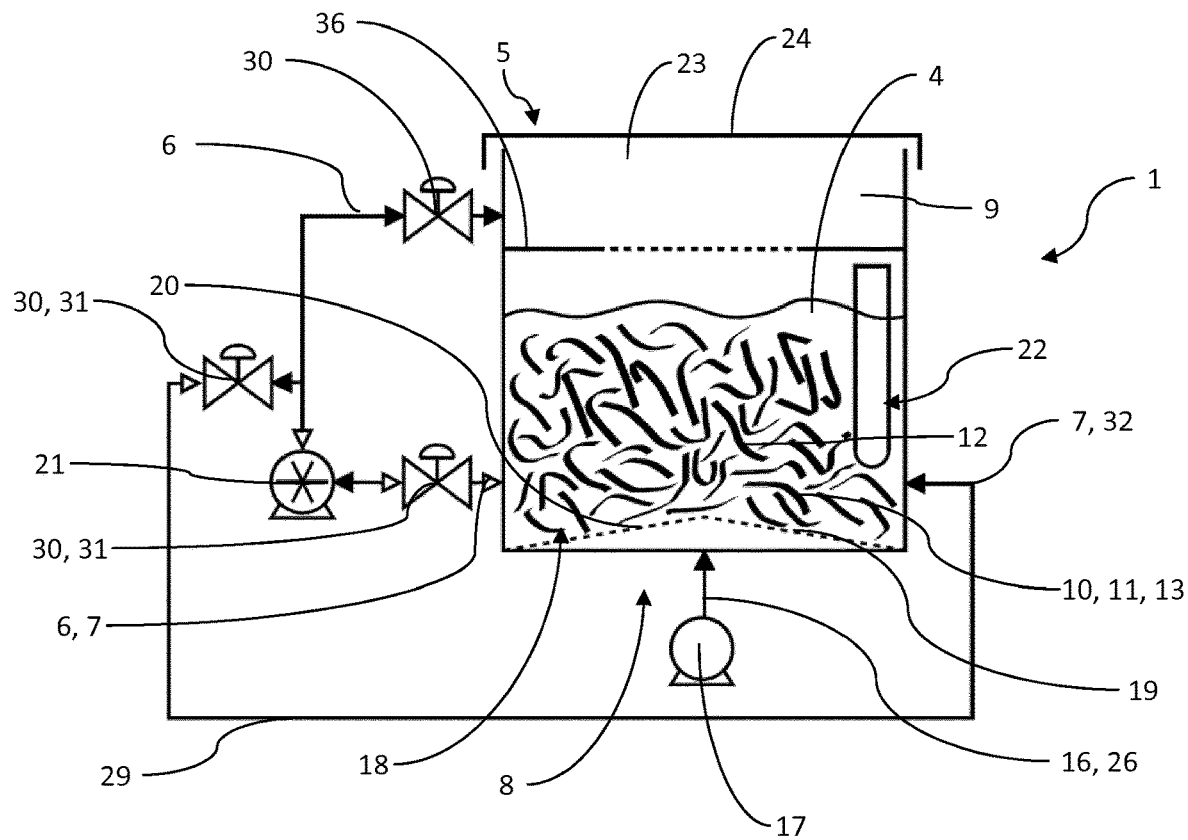
FIG. 1 an initial design variation for the bioreactor with several plastic chips joined together to form a cluster, which is then used as the carrier element.
Figure 2:
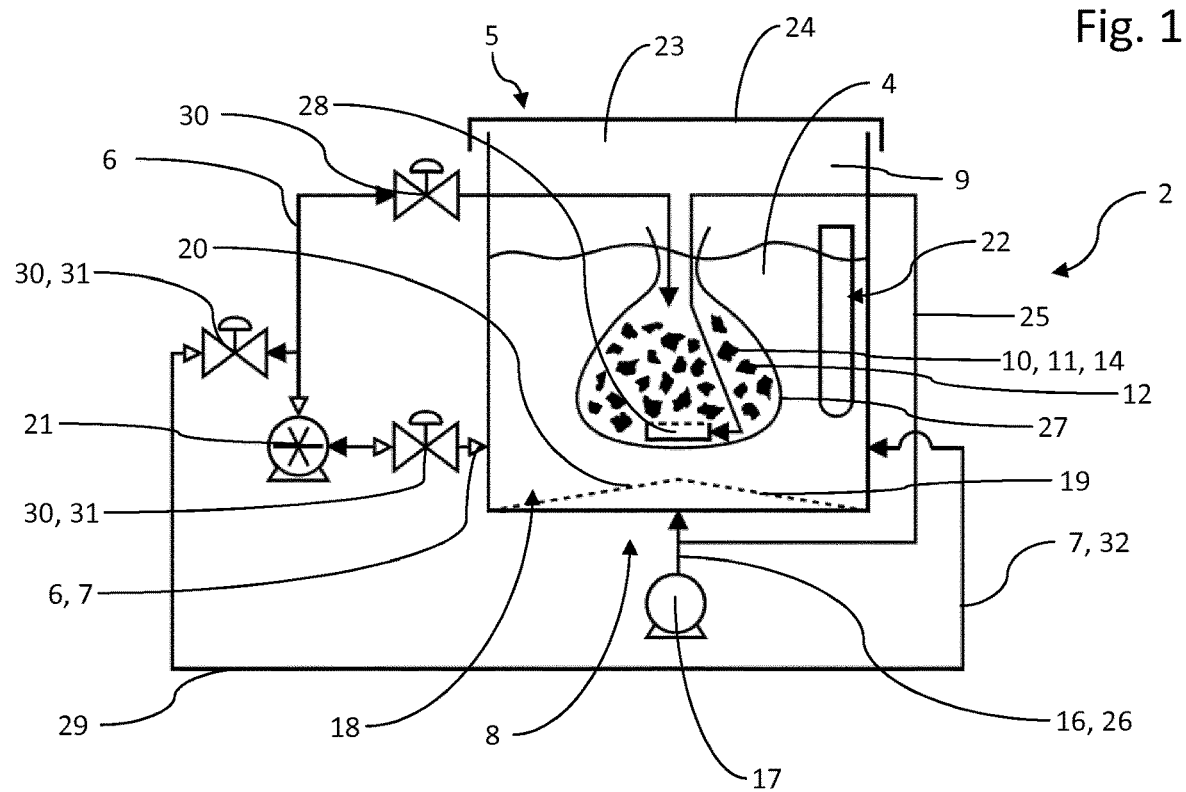
FIG. 2 a second design variation for the bioreactor with a number of carrier elements in the form of zeolite granulate, which are arranged inside a textile bag in the bioreactor's receiving chamber.
Figure 3:
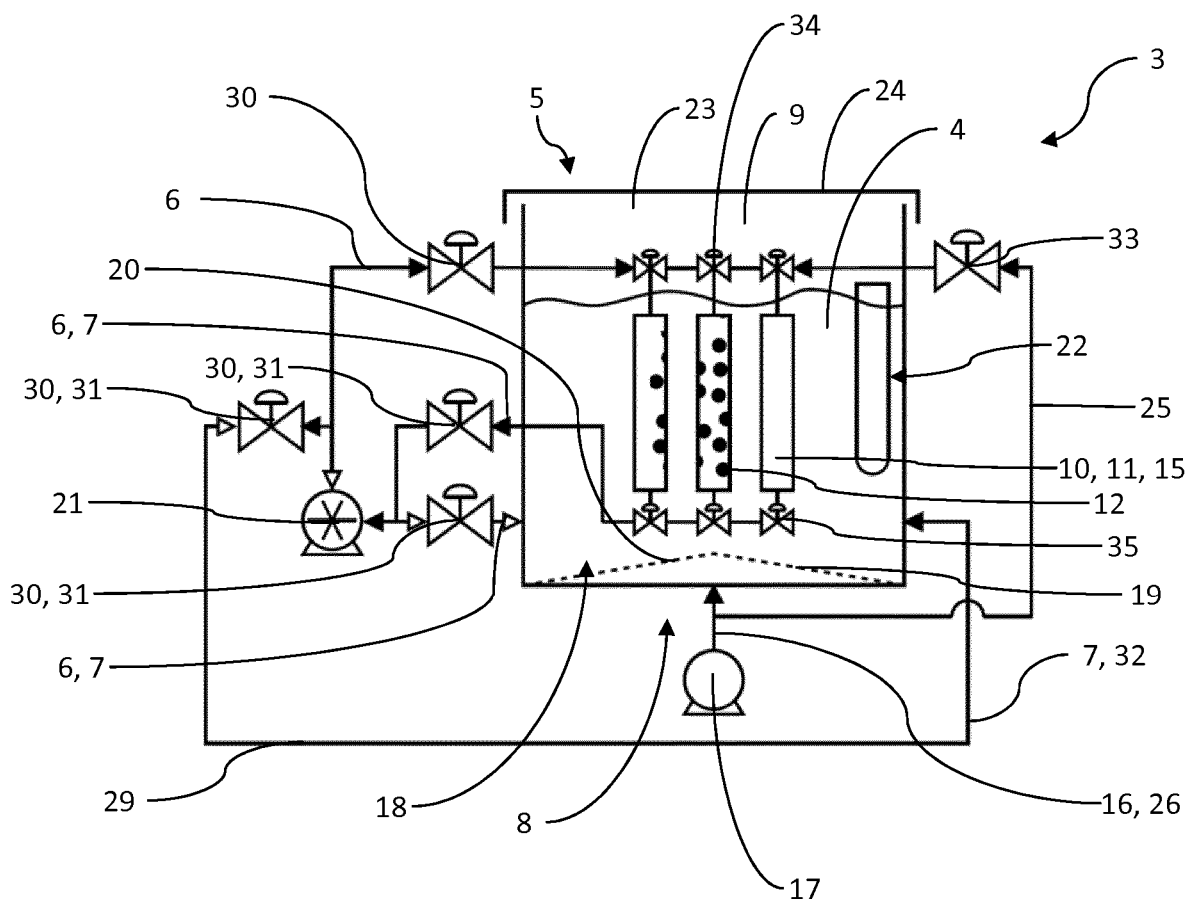
FIG. 3 a third design variation for the bioreactor with three carrier elements, each designed as porous tubes, which are connected parallel to each other in a line within the receiving chamber.

FIGS. 1 to 3 show three different design variations for the bioreactor, labelled 1, 2 and 3 respectively. Bioreactors 1, 2, 3 are designed to convert organic residues and/or waste into an organic nutrient solution with a relatively high proportion of plant-accessible mineralised nitrogen.

Through the use of bioreactors 1, 2, 3, it is possible to carry out a method for the production of such an organic nutrient solution in which a proportion of at least 10% of the total nitrogen content of the nutrient solution is accessible to plants. Further, the nitrate content of the plant-accessible mineralised nitrogen that is produced is higher than the ammonium content.

Bioreactors 1, 2, 3 feature a reaction tank 5, into which an input feed 6 and an output feed 7 open. Suspension 4 can be introduced into the reaction tank through the input feed 6 and the suspension can be discharged again through the output feed 7 after passing through the reaction tank 5.

Bioreactors 1, 2, 3 feature an aeration device 8, through which oxygen-preferably in the form of air—can be introduced into the reaction tank 5. In the design examples shown through FIGS. 1 to 3, the aeration device 8 is fitted with a compressor 17. A gas supply line 16 allows for oxygen (in the form of air) to be introduced into the reaction tank 5 through the compressor 17.

The three bioreactors 1, 2 and 3 differ in the use of different carrier elements 10, each of which is arranged inside a receiving chamber 9 in the reaction tank 5. The carrier elements 10 are position in the receiving chambers 9 in such a way that the carrier element 10 can be flushed using the suspension 4 introduced through the input feed 6. The suspension 4 may, for example, be an organic residual and/or waste material (as described above) and/or waste material (as described above), and/or an organic inoculation material (as described above). Further, the carrier elements 10 are also arranged in such a way that the oxygen introduced by the aeration device 8 flows around the carrier elements 10, preferably on all sides.

The carrier elements 10 have a particularly large surface area in relation to their volume. The surfaces of the carrier elements 10 are designed as settlement surfaces 11 for the formation of a biofilm 12, which is at least partly comprised of ammonifying and/or nitrifying bacteria. To this end, the settlement surfaces 11 are rougher than the inner side of the reaction tank wall. As such, the microorganisms in the biofilm 12 can adhere particularly well to the settlement surfaces 11 and grow there. This enables the ammonifying and/or nitrifying bacteria to form a biofilm 12 on the settlement surfaces 11, as these provide ideal conditions for growth.

The carrier elements 10 in the different design examples shown across FIGS. 1 to 3 are in part made of different materials or combinations of several materials.

The carrier elements 10 in the bioreactor 1 in FIG. 1 are made from plastic in the form of chips 13. Here, the chips 13 can be produced as waste products, for example, as part of the manufacturing process for plastic blanks. Here, it can be particularly advantageous for the chips to be made of a thermoplastic, such as polypropylene and/or polyethylene. In such cases, the large number of chips 13 can be arranged in an unordered manner within the receiving chamber 9 of the reaction tank 5. As the chips 13 have a curved settlement surface 11, which can be produced in chips 13 shaped as waves, spirals or ridges, it is easy to prevent the settlement surfaces 11 of individual chips 13 from adhering to one another. Adhering or contact between them is disadvantageous, because gas exchange and/or flushing can no longer be guaranteed and there is a reduced possibility of a biofilm forming. More specifically, this could lead to denitrification taking place.

For the bioreactor 2 shown in FIG. 2, the carrier elements 10 are designed as zeolite granulate 14. In order to prevent the granulate 14 from becoming trapped in poorly circulated or poorly ventilated areas of the receiving chamber 9, the carrier elements 10, here in granulate 14 form, are arranged in a collection unit 27 designed as a textile bag. The collection unit 27 can be attached to the receiving chamber by means of a hook or other suspension device. A further aeration device 28 is positioned within the collection unit 27 and releases there, allowing for the suspension 4 to be introduced directly into the collection unit 27. The collection unit 27 is designed with open pores, so that the suspension can flow out of the collection unit 27 and into the receiving chamber 9. The bypass gas line 25 branches off from a main gas line 26 which is connected to the aeration unit 8. This makes it possible to feed oxygen into the receiving chamber 9 at two different points without the need for a second compressor 17.

The bioreactor 3 shown in FIG. 3 has three carrier elements 10, each designed as a porous tube 15, which are then integrated parallel to one another in a pipe system within the receiving chamber 9. The porous tubes 15 are each connected to the input feed 6 and a gas supply line 16, itself designed as a bypass gas line 25. This allows, in particular, for suspension 4 and oxygen to be introduced into the porous tubes 15 at different times. In order to prevent the introduction of oxygen or suspension 4 into the porous tube 15 or several of the porous tubes 15, a shut-off valve 34 is positioned upstream of each porous tube 15 in the direction of flow of the input feed 6.

In order to increase the internal pressure in one porous tube 15 or in several porous tubes 15—especially independently of the other porous tubes 15—a further shut-off valve 35 is positioned after each porous tube 15 in the direction of flow of the suspension 4. By shutting off one valve 35, it is possible to prevent the suspension from escaping from the porous tube 15 via the output feed 7 that runs inside the receiving chamber 9. This allows the suspension 4 to escape instead through the pores in one of the tube walls and from there into the receiving chamber 9. As the porous tubes 15 are preferably designed to be expandable, increasing the pressure within a porous tube 15 can increase the size of the pores in the tube wall. The bioreactor 3 also has a further output feed 7, through which suspension 4 can be discharged from the receiving chamber 9 when the first output feed is shut off.

The aeration device 8 has an aeration plate 19, which is located at the floor 18 of the reaction tank 5 in bioreactors 1, 2, 3. The aeration plate 19 is connected to the compressor 17 through a gas supply line 16 and in particular through the main gas line 26. The aeration plate 19 has several evenly distributed aeration openings 20, through which oxygen can flow into the suspension 4.

Bioreactors 1, 2, 3 each have a pumping device 21, which can be designed specifically as a centrifugal pump or a circulating pump. Through the use of the pumping device 21, it is possible to pump the suspension 4 through the input feed 6 into the reaction tank 5 and to extract it from the reaction tank 5 through the output feed 7.

As such, bioreactors 1, 2, 3 feature a suspension circuit 29 consisting of the input feed 6 and output feed 7 and the reaction tank 5, in which the suspension 4 can be circulated using the pumping device 21. The pumping device 21 is set up in such a way that a suspension flow direction within the reaction tank 5 and/or within the various feeds in the reaction tank 5 and/or within the feeds of the bioreactors 1, 2, 3, are reversible. Combined with a number of shut-off valves 30, 21, 34, 35, the direction of flow within the reaction tank can be set and adjusted.

A shown in FIGS. 1 to 3, a bypass gas line 32 can branch off from the input feed 6 and on into the receiving chamber 9 in the reaction tank 5. If the direction of the suspension flow is reversed, one of the input feeds 6 can be converted into an output feed 7 and/or the bypass gas line 32 can be converted to an output feed 7. The function of the respective feeds is therefore dependent on the direction of flow that the suspension 4 takes, which in turn is determined by the pumping device 21. In general, however, it can be said that the input feeds 6 should open into the receiving chamber 8 in the reaction tank 5 at above or (at least) at the same level as the output feeds 7. This ensures more effective circulation of the suspension within the reaction tank 5.

In order to remove the carrier element 10 easily from the receiving chamber 9, the bioreactors 1, 2, 3 feature an opening 23 on the top side of the reaction tank 5. Through the use of a sealing unit 24, designed as a lid, this opening 23 can be sealed liquid-tight and/or pressure-tight while the bioreactors 1, 2, 3 are in use.

The bioreactor 1 features a dividing unit 36 in the upper third of the receiving chamber 9, which can be used to divide the suspension 4 into several independent streams. This allows, first, for the division of solids that may otherwise adhere to one another and, second, provides for additional aeration of the suspension. The dividing unit 36 can be designed in the form of a dividing plate, for example. Further, the dividing unit 36 can also be used as part of the other design variations shown in FIGS. 2 and 3, or combined with features from other additional claims.

The bioreactors 1, 2, 3 are also fitted with a heating device 22, through which the receiving chamber 9 and/or the suspension 4 contained within it can be heated to a desired temperature.

As shown in FIG. 3, it may be necessary in some cases to install a shut-off valve 33 in the bypass gas line 25. This can prevent oxygen from being introduced into the receiving chamber 9 in the reaction vessel 5, while at the same allowing for aeration through the aeration plate 19.

To produce a biofilm 12 that is at least partially made up of ammonifying and/or nitrifying bacteria, a partly water-based suspension should be prepared from a particulate organic inoculation material. Worm excrement or a worm-processed soil can be used as such inoculation material. Other possible inoculation materials have been described in greater detail above. In principle, it can be said that all organic substances that contain proteolytic soil bacteria may be suitable for use as inoculation materials.

For optimum biofilm formation, the inoculation material should be brought into contact with the carrier element 10 through circulation and agitation caused by air injected through it. Organic inoculation material shows increased levels of soil bacteria, mucus and other proteins and inorganic minerals, which are then bound together with dead bacterial material. These ingredients help the bacteria to adhere to the carrier element 10 and therefore work to promote the formation of a biofilm. Additionally, they also serve as nutrients for the bacteria. This results in a carrier element 10 with a diverse, qualitatively and quantitatively variable and adjustable bacterial culture that can consist of a variety of soil bacteria, including ammonifying and nitrifying bacteria.

After the biofilm 12 has been formed on the surface of the carrier element 10, the carrier element 10 can be removed from the first reaction tank 5 and transferred to another reaction tank 5. As such, organic residual and/or waste material can be converted into an organic nutrient solution through the use of the biofilm. However, it is also possible that the inoculation step and the incubation step are carried out in the same reaction tank 5. Here, it is recommended that the inoculation material is removed from the reaction tank 5 before organic residual and/or waste material is added.

The invention therefore relates to a bioreactor 1, 2, 3 and its use for the conversion of organic residual and/or waste materials into an organic nutrient solution with a proportion of at least 10% plant-accessible mineralised nitrogen relative to the total nitrogen content of the nutrient solution, with a reaction tank 5; where the reaction tank 5 has an input feed 6, through which suspension 4 can be introduced into the reaction tank 5; and where the reaction tank 5 has an output feed 7, through which the suspension 4 can be discharged from the reaction tank; and where the design also features an aeration device 8 to aerate the suspension 4 and/or a carrier element 10 positioned inside the reaction tank 5; where the carrier element 10 has at least one inner and one outer settlement surface 11 on which ammonifying and/or nitrifying bacteria can settle, forming a biofilm 12.

LIST OF REFERENCE NUMBERS 1,2,3 Bioreactor
4 Suspension
5 Reaction tank
6 Input feed
7 Output feed
8 Aeration device
9 Receiving chamber
10 Carrier element
11 Settlement surface
12 Biofilm
13 Chips
14 Granulate
15 Porous tube
16 Gas supply line
17 Compressor
18 Floor of the reaction tank
19 Aeration plate
20 Aeration openings
21 Pumping device
22 Heating device
23 Opening
24 Sealing unit
25 Bypass gas line
26 Main gas line
27 Collection unit
28 Additional aeration device
29 Suspension circuit
30 Shut-off valve
31 Shut-off valve
32 Bypass feed
33 Shut-off valve (air)
34 Shut-off valve in reaction tank
35 Shut-off valve in reaction tank
36 Dividing unit

The invention claimed is:

1. A bioreactor (1, 2, 3) for conversion of organic residual and/or waste materials into an organic nutrient solution with a proportion of at least 10% of plant-accessible mineralized nitrogen relative to a total nitrogen content of the nutrient solution, the bioreactor comprising:
   a reaction tank (5) having an input feed (6) through which suspension (4) is introducible into the reaction tank (5); and
   the reaction tank (5) has an output feed (7) through which the suspension (4) is dischargeable from the reaction tank (5);
   an aeration device (8) through which oxygen is introduced into the reaction tank (5) and the suspension (4) contained therein;
   a carrier element (10) with a settlement surface (11) configured for formation of a biofilm (12) of microorganisms positioned within a receiving chamber (9) inside the reaction tank (5);
   the carrier element (10) is at least one of flushable or rinseable with the previously introduced suspension (4) and oxygen; and
   the carrier element (10) has a surface-to-volume ratio that is greater than a surface-to-volume ratio of the receiving chamber (9).

2. The bioreactor (1, 2, 3) according to claim 1, further comprising a pump (21) through which the suspension (4) is adapted to be pumped through the input feed (6) into the reaction tank (5) and through the output feed (7) out of the reaction tank (5).

3. The bioreactor (1, 2, 3) according to claim 1, wherein at least one of: the bioreactor (1, 2, 3) has a number of the carrier elements (10), which can move relative to one another; or a number of chips (13) are provided, and the chips (13) are arranged in an unordered manner inside the reaction tank (5) so that a tangling of the chips (13) occurs and where each of the chips (13) has a length of 2 cm to 10 cm, a width of 0.5 cm to 1.5 cm, and a depth of 50 µm to 500 µm.

4. The bioreactor (1, 2, 3) according to claim 1, wherein the carrier element (10) comprises at least one porous tube (15) and the at least one porous tube (15) is positioned at least one of transversely from or parallel to a flow direction of the oxygen introduced into the reaction tank (5) or transversely from or parallel to the flow direction of the suspension (4) introduced into the reaction tank (5); and oxygen is introduced through the at least one porous tube (15) via a gas supply line (16).

5. The bioreactor (1, 2, 3) according to claim 1, wherein the carrier element (10) comprises zeolite granulate (14) positioned inside a collection unit (27) that is placed inside the reaction tank (5); and an additional aeration device (28) is positioned on a floor of the collection unit (27), through which oxygen is introduced into the zeolite granulate (14) and the additional aeration device (28) is connected to a bypass gas line (25) that branches off from a main gas line (26).

6. A method for preparation of an organic nutrient solution with a proportion of at least 10% plant-accessible, mineralized nitrogen relative to a total nitrogen content of the organic nutrient solution, the method comprising the following steps:
   inoculating a carrier element (10) in the bioreactor (1, 2, 3) according to claim 1 using an inoculation material that contains at least one of an ammonifying or nitrifying bacteria,
   forming a biofilm (12) on the carrier element (10) with the at least one of the ammonifying or nitrifying bacteria,
   incubating at least one of an organic residual or waste material with the biofilm (12), and in the reaction tank (5), where the at least one of the ammonifying or nitrifying bacteria convert organically bound nitrogen in the at least one of the residual or waste material into mineralized nitrogen, and
   introducing oxygen into at least one of the reaction tank (5) or the carrier element (10) during the process of carrying out one or more of these steps.

7. The method according to claim 6, wherein a proportion of organic material in the at least one of the organic residual or water material falls within 5% to 60%; a carbon/nitrogen ratio of the at least one of the organic residual or waste material is 11 or less; a total nitrogen proportion relative to the total contents of the at least one of the organic residual or waste material is at least 0.3%; or a proportion of nitrate-bound nitrogen relative to the total plant-accessible nitrogen content of the at least one of the organic residual or waste material is less than a proportion of ammonium-bound nitrogen.

8. The method according to claim 6, wherein the incubation step comprises at least one of an ammonification step or a nitrification step, where organically bound nitrogen from the at least one of the organic residual or waste material is converted into ammonium during the ammonification step by the ammonifying bacteria in the biofilm, and where ammonium is converted into nitrate during the nitrification step by the nitrifying bacteria in the biofilm (12), and these steps continue until the organic nutrient solution contains more nitrate than ammonium.

9. The method according to claim 6, wherein at least one porous tube (15) is used as the carrier element (10), in which oxygen and the at least one of the residual or waste material are introduced into the at least one porous tube (15) at separate points during the process, and an internal pressure inside the at least one porous tube is varied during at least one of the inoculation step or the incubation step by at least one of increasing the flow of at least one of the inoculation material or the at least one of the residual or waste material through the at least one porous tube (15) for a set period of time, or by increasing a volume of oxygen flow through the at least one porous tube (15) for a set period of time.

10. An organic nutrient solution produced by a method according to claim 6, wherein there is proportion of at least 25% mineralized plant-accessible nitrogen relative to a total nitrogen content of the organic nutrient solution; a proportion of nitrogen in the plant-accessible mineralized nitrogen is higher than a proportion of ammonium; the mineralized plant-accessible nitrogen is converted from organically bound nitrogen; and the organic nutrient solution is free from industrially produced mineral fertilizer.

11. A substrate material for cultivation of plants, the substrate material comprises a porous tube (15) acting as a carrier element (10); the substrate material is adapted for use as an anchoring material in a hydroponic cultivation system; the plants are at least partially in direct contact with an outer side of the carrier element (10) of the substrate material through their roots; an organic nutrient solution according to claim 10 is passed through the carrier element; the organic nutrient solution is at least one of diffused or pressed through pores in the carrier element wall from an inner side of the carrier element (10) to an outer side of the carrier element (10) so that the roots of the plants that are at least partially in contact with the outer side of the carrier element are able to absorb the mineralized plant-accessible nitrogen.

12. A substrate material for cultivation of plants, the substrate material comprises a porous tube (15) acting as a carrier element (10), the substrate material is mixed through a plant soil; an organic nutrient solution according to claim 10 is passed through the carrier element (10), the organic nutrient solution is at least one of diffused or pressed through pores in the carrier element wall from an inner side of the carrier element (10) to an outer side of the carrier element (10).

13. A method for producing a substrate material for cultivation of plants, comprising the following steps:
    inoculating a carrier element (10) in the bioreactor (1, 2, 3) according to claim 1 using an inoculation material that contains at least one of an ammonifying or nitrifying bacteria,
    forming a biofilm (12) on the carrier element (10) with the at least one of the ammonifying or nitrifying bacteria, and
    introducing oxygen into at least one of the reaction tank (5) or the carrier element (10) during a process of carrying out one or more of these steps.

14. A set-up comprising the bioreactor according to claim 1 and an inoculating material designed to inoculate the carrier element (10) and to form a biofilm (12) with at least one of an ammonifying or nitrifying bacteria.

15. A substrate material for cultivation of plants, the substrate material comprises a porous tube (15) acting as a carrier element (10); the substrate material forms an anchoring material in a hydroponic cultivation system; where the plants are at least partially in direct contact with an outer side of the carrier element (10) of the substrate material through roots of the plants; and at least one of an organic residual or waste material is passed through the carrier element (10); nitrogen in the at least one of the residual or waste material that has been organically bound by bacteria in a biofilm (12) is converted into an organic nutrient solution including mineralized nitrogen in a nitrogen solution that is at least one of diffused or pressed through pores in a carrier element wall from an inner side of the carrier element (10) to an outer side of the carrier element (10); and the roots of the plants that are at least partially in contact with the outer side of the carrier element are able to absorb the mineralized nitrogen which is plant-accessible.

* * * * *